United States Patent
Markus

[11] Patent Number: 5,843,043
[45] Date of Patent: Dec. 1, 1998

[54] SYRINGE AND PROCESS FOR DISPENSING TREATMENT FLUID

[76] Inventor: George Markus, 7 S. Applewood Ct., Fairfield, Ohio 45014

[21] Appl. No.: 823,613

[22] Filed: Mar. 25, 1997

[51] Int. Cl.⁶ .................................................. A61M 5/00
[52] U.S. Cl. ............................................. 604/239; 604/275
[58] Field of Search .................................. 604/239, 218, 604/275, 187, 212

[56] References Cited

U.S. PATENT DOCUMENTS

| | | |
|---|---|---|
| 1,155,848 | 10/1915 | Tyrell . |
| 1,567,009 | 12/1925 | Sterrit . |
| 1,640,928 | 8/1927 | Donavan . |
| 1,775,329 | 9/1930 | Sprague . |
| 2,869,546 | 1/1959 | Cantor ................................. 604/275 X |
| 3,109,427 | 11/1963 | Davidson ............................. 604/275 X |
| 3,225,763 | 12/1965 | Waterman ................................ 604/275 |
| 3,557,788 | 1/1971 | Swartz . |
| 4,846,801 | 7/1989 | Okuda et al. . |
| 4,923,448 | 5/1990 | Ennis, III . |
| 4,968,306 | 11/1990 | Huss et al. . |
| 5,310,091 | 5/1994 | Dunning et al. . |
| 5,609,581 | 3/1997 | Fletcher et al. ........................ 604/239 |

*Primary Examiner*—John D. Yasko
*Attorney, Agent, or Firm*—Donald D. Gillette

[57] ABSTRACT

A syringe that includes a barrel with a removable, tapered nozzle having a rounded front end to facilitate its entering a body cavity without the necessity of puncturing the skin. The nozzle has side openings through which the treatment fluid can be expelled against the wall defining the body cavity. The syringe also has a plunger slidably movable in the barrel and provided with a front end shaped to substantially fill the nozzle so that, when the plunger is pushed fully forward, it will displace a selected amount of the treatment fluid safely through the side openings onto an adjacent wall surface of a body cavity. The nozzle is removably attached to the barrel so that it can be removed to place the selected amount of a treatment fluid in a chamber bounded by the barrel, the nozzle, and the front end of the plunger.

19 Claims, 7 Drawing Sheets

SYRINGE AND PROCESS FOR DISPENSING TREATMENT FLUID

BACKGROUND OF THE INVENTION

1. Field of the Invention

This invention relates to the field of dispensing a selected amount of a treatment fluid into an existing body cavity of a patient to treat an area of the side wall of the cavity close to the point of entry. In particular, the invention relates to a syringe that includes a barrel, a removable, tapered nozzle having a rounded front end that can enter the body cavity without the necessity of puncturing the skin and has side openings through which the treatment fluid can be expelled, and a plunger that is slidably movable in the barrel and has a front end shaped to substantially fill the nozzle and thereby displace a selected amount of the treatment fluid safely through the slots onto an adjacent wall surface of a body cavity. The nozzle is removably attached to the barrel so that it can be removed to place the selected amount of a treatment fluid in a chamber bounded by the barrel, the nozzle, and the front end of the plunger.

2. The Prior Art

It is well-known to dispense a treatment fluid into an existing body cavity of a patient by way of a syringe equipped with a safety nozzle having a rounded end that can enter the cavity without creating a puncture in a surface membrane, such as would be done by a hypodermic needle, and can dispense treatment fluids including those of relatively high viscosity, such as ointments, creams, emulsions, emollients, salves, or the like. High viscosity fluids are those in which the surface is capable of retaining a given non-planar shape for an appreciable time before returning to a planar condition.

However, such syringes have all had shortcomings, particularly in trying to dispense a specific volume of the treatment fluid to the proper area on the side wall of the cavity adjacent the nozzle. Dispensing only the specific volume and directing it to the side wall area needing treatment are desirable and even important in many instances. For example, being able to control the amount of high-viscosity fluid is especially important in cases in which the benefit provided by the treatment fluid must be balanced against possible adverse side effects.

Some rounded nozzles have been formed with an opening only at the end and would thus project the treatment fluid farther into the cavity, not against the adjacent side wall. Therefore, such syringes might not medicate the affected side wall area at all. Other syringes have had side apertures through which the treatment fluid is more likely to be dispensed directly toward the side wall area requiring treatment but are not provided with removable nozzles that allow access to a chamber to receive a selected amount of high-viscosity treatment fluids.

In U.S. Pat. No. 1,155,848, Tyrell discloses a rectal syringe, the nozzle of which is cylindrical and has exit holes in its side wall. Instead of a plunger, the fluid to be injected is a liquid held in a water bag that is squeezed. No way is disclosed to dispense a high-viscosity fluid nor a specific amount of a treatment fluid.

Sterrit discloses a rubber nozzle attached to the side wall of a hot-water bottle in U.S. Pat. No. 1,567,009. Pressure by the user downward on the nozzle that has openings in its side wall releases a valve and allows liquid from the hot-water bag to be injected into the user, but without regard to whether or not all of the fluid is directed toward an affected part of the side wall of the cavity needing treatment.

U.S. Pat. No. 1,640,928 to Donovan shows a syringe that has a small, cylindrical body and a large, pear-shaped nozzle through which to inject fluid into a patient's rectum. The syringe has a plunger in the cylindrical body, but the plunger does not extend into the nozzle, and no attempt is made to inject every bit of the fluid in the cylindrical body.

In U.S. Pat. No. 1,775,329 Sprague describes a one-piece syringe made of hard rubber for injecting a viscous fluid, or ointment, into the rectum. The nozzle is slightly tapered and has two sets of pairs of side ports and a tapered section joining the nozzle to a larger diameter body that holds the viscous fluid. The plunger that forces the fluid out is cylindrical and has a diameter smaller than the internal diameter of the body, or barrel, of the syringe and much larger than the nozzle. The front end of the plunger does not fit either the nozzle or the taper at the forward end of the body and, therefore, would not force out all of the fluid or ointment.

U.S. Pat. No. 3,557,788 to Swartz shows a fluid dispenser that has no plunger and, therefore, no way to expel all of the fluid contained in the body of the dispenser. Instead, the body of the dispenser is made of accordion-pleated, collapsible material that can be forced to collapse to dispense fluid through a cylindrical nozzle that has openings along its side and at its end.

Okuda et al. shows a cylindrical syringe in U.S. Pat. No. 4,846,801. The syringe has a cylindrical body, or barrel, formed with an integral tapered nozzle, an external cap, and a plunger with a forward end that fills the nozzle to cause some of the medicament in the syringe to be expelled into the cap first and the remainder into the patient later. The nozzle is not removably attached to permit a precise amount of fluid to be loaded into a chamber at the juncture of the nozzle and the barrel.

In U.S. Pat. No. 4,923,448, Ennis III shows a syringe to dispense atomized liquid. The syringe has a nozzle formed integrally with the cylindrical part of the body and provided with means to atomize liquid as it is expelled. The plunger does not extend into the nozzle and does not necessarily dispense all of the liquid.

In U.S. Pat. No. 4,968,306, Huss et al. disclose an elongated catheter that has no plunger.

In U.S. Pat. No. 5,310,091 Dunning et al. provide a dispenser of two fluids from two in-line spaces simultaneously by way of a concentric orifice. The plunger does not fit into the nozzle to dispense all of a measured amount of fluid.

OBJECTS AND SUMMARY OF THE INVENTION

It is an object of this invention to provide means for dispensing a specific amount of a treatment fluid, against the side wall of a body cavity and directly upon a fissure, ulceration, eczema or other pathological condition in order to provide controlled medical treatment of the affected part of the side wall.

Another object is to provide a process for directing a specific amount of a treatment fluid against a specific region of the side wall of a body cavity to treat a pathological condition of that region of the side wall.

Those who are skilled in the technology with which this invention deals will recognize further objects after studying the following description.

In accordance with this invention, a syringe for injecting a selected amount of a treatment fluid into a body cavity includes a cylindrical barrel that has a certain internal cross-sectional configuration and size at one end and a generally shell-like, tapered nozzle removably attached to the barrel at that end. The front end of the nozzle is smoothly rounded, i.e., it has no sharp edges or points, and is small enough to enter the body cavity easily. The back end of the nozzle, which is removably joined to the front end of the barrel, is larger than the rounded front end of the nozzle and has an intersecting surface that fits against the front end of the barrel. At that surface, both the nozzle and the barrel have the same internal cross-sectional configuration and size. The nozzle has longitudinal slots around its side wall through which to dispense treatment fluid directly to pathologically affected areas of the wall surface of the body cavity. The syringe further includes a plunger that is slidable in the barrel and fits fluid-tight therein.

In order to get the treatment fluid into a space within the syringe, the nozzle is removed, thereby opening a chamber bounded by the inner surface of the nozzle, the front end of the plunger and the portion of the barrel immediately adjacent the nozzle. This chamber is graduated and is large enough to hold at least the selected quantity of treatment fluid. Since the size of the chamber is determined, in part, by the position of the plunger within the barrel, the chamber may be enlarged, at the time it is being loaded with the treatment fluid, by drawing the plunger away from the front end of the barrel. When the selected quantity of treatment fluid has been put into the chamber, the nozzle is reattached to the front end of the barrel.

The shape of the front end of the plunger substantially conforms to the shape of the inner surface of the nozzle so that when the plunger is pushed fully forward, it fills the nozzle, thereby expelling through the slots in the nozzle all of the selected quantity of treatment fluid placed in the chamber.

The invention will be described in greater detail in connection with the drawings, in which like reference numbers in different figures indicate the same item.

DETAILED DESCRIPTION OF A PREFERRED EMBODIMENT

Figure 1:
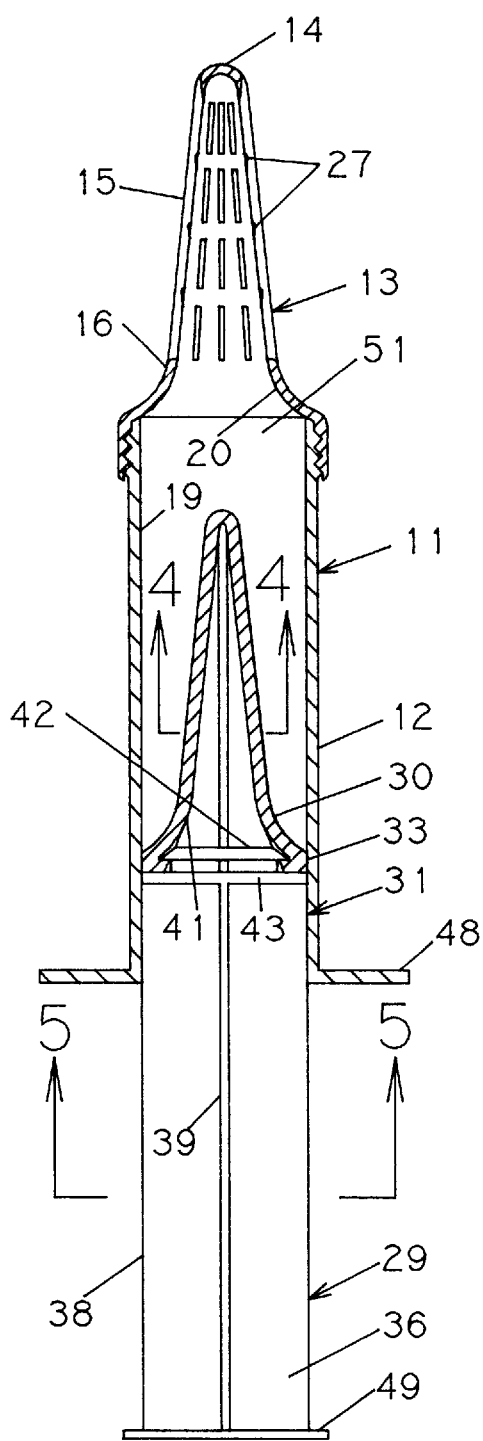
FIG. 1 is a side view of a syringe according to the invention with parts of the syringe broken away to show its internal components.
Figure 2:
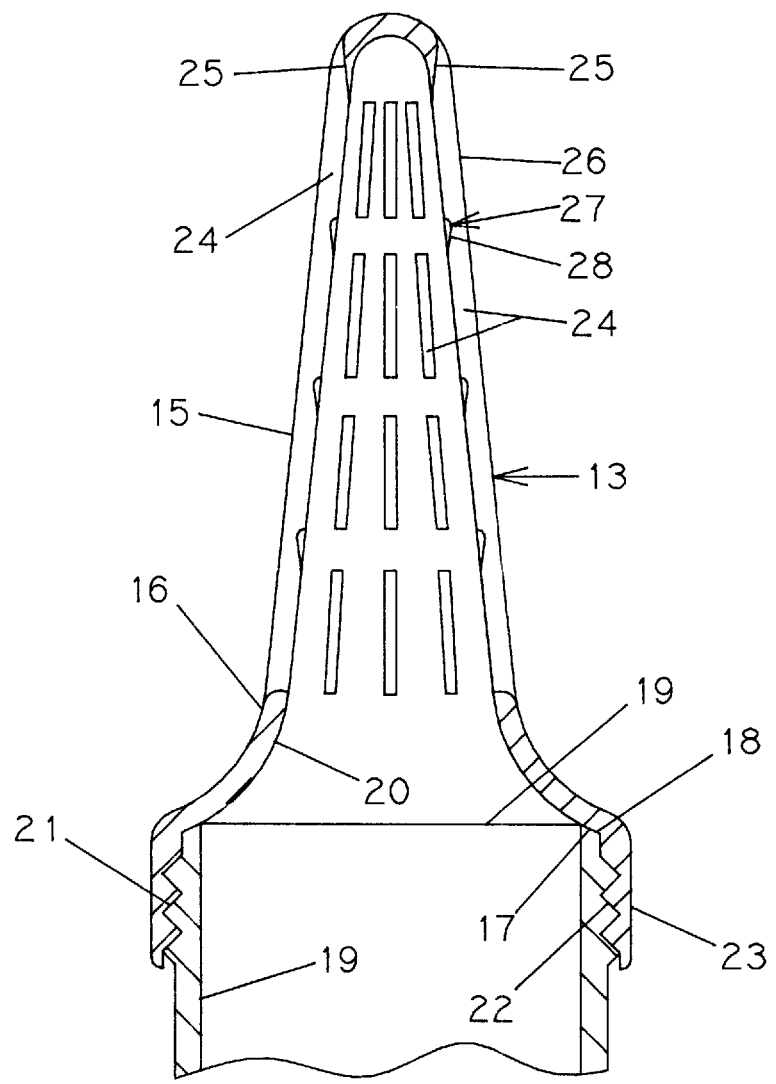
FIG. 2 is an enlarged cross-sectional view of a fragment of the nozzle in FIG. 1.
Figure 3:
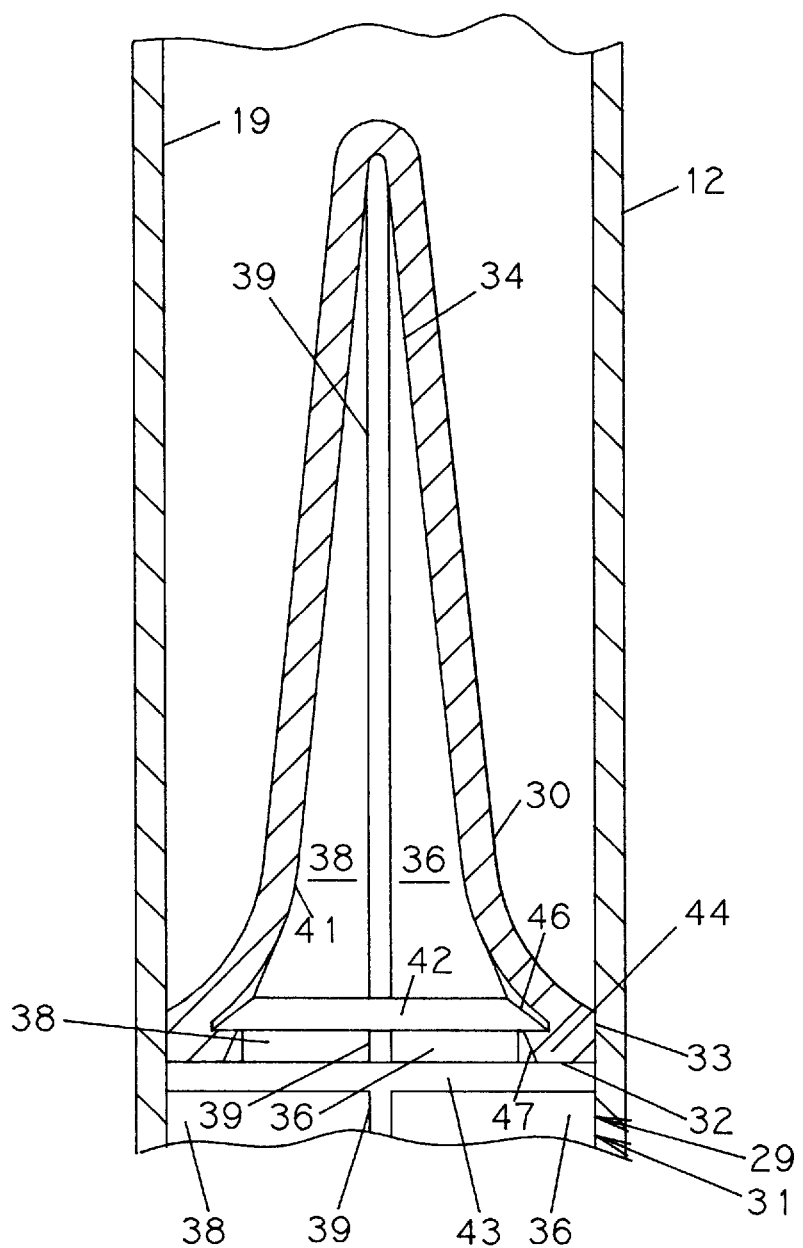
FIG. 3 is an enlarged cross-sectional view of a fragment of the barrel and the plunger in FIG. 1.

The syringe 11 in FIGS. 1–3 includes a barrel 12 and a nozzle 13, both shown in cross section. In this embodiment, the nozzle is a shell that has a tapered wall 15 of relatively uniform thickness and a small, generally hemispherically rounded front end 14 that has no outwardly facing sharp points or edges. The taper of the part of the wall between the rounded front end and a location 16 is substantially linear. At the location 16, the nozzle flares out, thereby providing a form of stop that prevents a person using the syringe 11 from pushing the nozzle too far into a body cavity or opening. The nozzle also includes a generally annular or frusto-conical surface 17 that intersects a front end surface 18 of the barrel 12. The configuration of this front end surface matches the configuration of the intersecting surface 17, allowing these intersecting surfaces to fit fluid-tight against each other and creating a fluid-tight junction between the nozzle and the barrel. The barrel 12 has an inner surface 19 and the nozzle 13 has an inner surface 20 and both the nozzle and the barrel may be molded of thermoplastic material, one example of which is polypropylene.

To facilitate joining the nozzle 13 fluid-tight but removably to the barrel 12, the barrel has an external thread 21 in the region of its front end surface 18. The nozzle 13 has a matching internal thread 22 at its larger end 23, and an external gripping surface comprising smooth, longitudinal ridges. Along the tapered wall 15 of the nozzle are slots 24 parallel to the axis of the nozzle 13 and angularly spaced apart around the axis to allow treatment fluid to be dispensed in virtually all directions perpendicular to the axis to be sure that the treatment fluid will be applied to any pathologically affected region of the wall surface of the cavity adjacent the nozzle. The end 14 is preferably closed to minimize ejection of the treatment fluid farther into the body cavity. Each of the slots has, at its end closer to the rounded end 14, a surface 25 substantially parallel to the axis of the nozzle 13 so that the nozzle can be separated from its mold by direct axial movement. The outwardly facing end edges of the end surfaces 25, and of the longitudinal side surfaces of the slots are preferably slightly rounded to prevent unnecessary discomfort or injury to the patient. Thus, the slots 24 are slightly wider at their intersections with the external surface 26 of the nozzle than they are at the inner surface 20.

In this embodiment, the slots 24 are interrupted by bridges 27 that stiffen the nozzle 13. In keeping with making it easy to remove the nozzle from its mold, the bridges have surface portions 28 that are substantially parallel to the axis of the nozzle. This requires that the thickness of the bridges, as measured radially from the axis of the nozzle, be less than the full wall thickness of the nozzle. The fact that outwardly facing surfaces of the bridges are thus inset from the external surface 26, in addition to the fact that the edges of the bridges are somewhat rounded, keeps the bridges from irritating the surface of the cavity into which the nozzle 13 is inserted to dispense a treatment fluid in accordance with this invention.

Within the syringe is a movable member, or plunger, 29 that comprises a front part 30 and an actuator 31 in this embodiment. The part 30 will be referred to as the displacement part because it displaces the treatment fluid as the plunger is moved forward. The shape of the front part 30 is the converse of the shape of the inner surface 20 of the nozzle so that, when the plunger is pushed to the forward end of its range of travel, the front part of the plunger fills up the nozzle and leaves no empty space that might retain fluid that should be dispensed through the slots 24. In this embodiment, the displacement part 30 is hollow and is molded of elastomeric material that has a durometer of 40–60 Shore D to allow it to seal against the inner surface 19 of the barrel while still allowing the plunger to slide freely. At the rear end 32 of the elastomeric displacement part 30, the external surface 33 may be slightly larger than the internal surface 19 of the barrel 12 in order to apply enough radially outward pressure against the surface 19 to form a fluid-tight seal.

Figure 4:
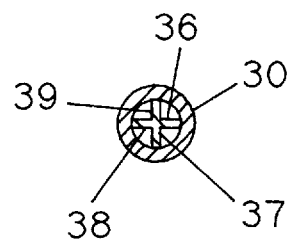
FIG. 4 is a cross-sectional view of the plunger at the parting line 4—4 in FIG. 1.
Figure 5:
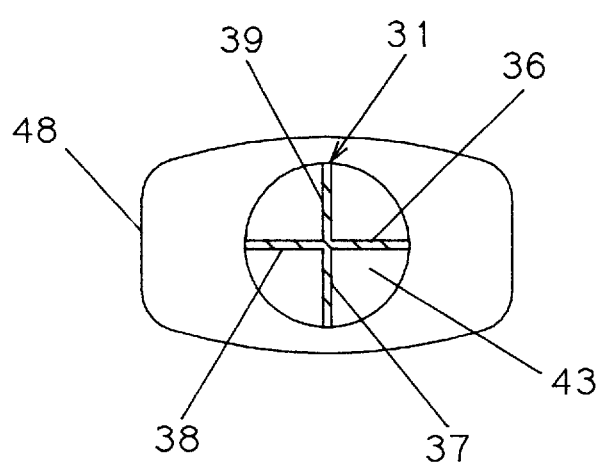
FIG. 5 is a cross-sectional view of the syringe at the parting line 5—5 in FIG. 1.

The actuator 31 is the means for applying longitudinal pressure to the displacement part 30 to move it back and forth in the barrel 12 and is long enough to push the displacement part fully into contact with the entire internal surface 20 of the nozzle 13. Since the displacement part 30 is somewhat soft, the forward end 34 of the actuator 31 extends into contact with the internal surface of the forward end of the displacement part 30 to serve as stiffening means. While the forward end 34 could be shaped to fill the inner surface of the displacement part 30, in this embodiment compromises four longitudinal ribs 36–39 arranged in a cruciform configuration, as shown in the cross-sectional view in FIG. 4, and tapered to conform to the inner surface 41 of the displacement part.

The actuator has two transverse flanges 42 and 43 axially spaced a short distance apart, and the rear end of the displacement part 30 has an inwardly directed flange 44 that has a thickness substantially equal to the distance between the flanges 42 and 43. The flange 42 has a frusto-conical surface 46 with a smaller diameter at its front end to facilitate forcing the flange 44 over it, and the flange 44 has a converse frusto-conical surface 47 with a larger diameter at its rear end to facilitate fitting over the flange 42. The flange 43 cooperates with the flange 42 in holding the flange 44 and in applying forward pressure to the displacement part 30 to expel the treatment fluid through the nozzle 13.

Figure 6:
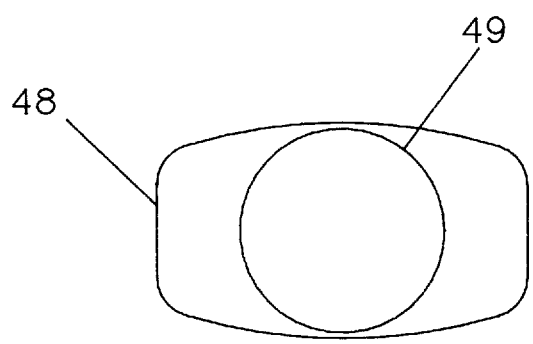
FIG. 6 is an end view of the syringe in FIG. 1.

The ribs 36–39 are not limited to the forward portion of the actuator but also extend between the transverse flanges 42 and 43 and beyond the flange 43 through the main part of the barrel 12. Within the barrel, the ribs 36–39 extend radially outwardly, substantially to the inner surface 19 of the barrel 12, to serve as guide means for the actuator 31 and to hold the plunger 29 aligned with the barrel 12 in moving the displacement part 30 back and forth. At the rear end of the barrel is a barrel flange 48, and at the rear end of the ribs 36–39 is an end flange 49. A person using the syringe can draw the plunger 29 rearwardly, to the position shown or even farther to the rear, by pulling the flange 49 and pushing the flange 48. By pushing the flange 49 toward the flange 48, the plunger 29 can be moved forward, ultimately far enough to press the displacement part 30 against the inner surface 20 of the nozzle 13. The flanges 48 and 49 are shown in the end view of the syringe in FIG. 6.

In the operation of the syringe 11, the nozzle 13 is unscrewed from the barrel to obtain access to a chamber 51, part of which may be within the nozzle and part within the front part of the barrel 12 ahead of the displacement part. Once the chamber is open, it is easy to place a selected quantity of treatment fluid in it. In particular, this makes it possible to load a high-viscosity treatment fluid in the chamber. The chamber may be expanded to its largest size (for a given syringe) by pulling the flange 49 away from the flange 48 to move the displacement part 30 away from the front end 18 of the barrel. The selected amount of treatment fluid to be dispensed to a patient is placed in this chamber and the nozzle is screwed back on the barrel.

If it is desired to expel air in the chamber 51, that may then be done by moving the end flange 49 toward the barrel flange 48. When the chamber 51 no longer contains any undesired air, any small amount of treatment fluid that has been expelled along with the air can be smeared on the external surface 26 of the nozzle 13, and the nozzle may then be inserted in the affected body cavity of the patient. Then, by pushing the plunger forward as far as it will go, thereby causing the external surface of the displacement part 30 to be brought fully into contact with the internal surface of the nozzle 13, all of the selected amount of treatment fluid will be displaced through the slots 24 directly against the affected surface to be treated. The only part of the treatment fluid remaining attached to the syringe 11 may be a thin film on the external surface of the displacement part 30 and the internal surface 20 of the nozzle and an inconsequential amount in the slots 24.

While the whole syringe 11 may be disposed of after dispensing the treatment fluid, it is also easy to separate the nozzle 13 from the barrel 12 and dispose of the nozzle, alone. In either case, the nozzle 13 must first be withdrawn from the body of the patient without retracting the plunger 29 from its fully forward position so as not to draw any material from the body of the patient through the slots 24 and into the nozzle. After the nozzle 13 is out of the patient's body, the whole syringe can be disposed of or the nozzle removed and disposed of alone while retaining the barrel and plunger.

Figure 7:
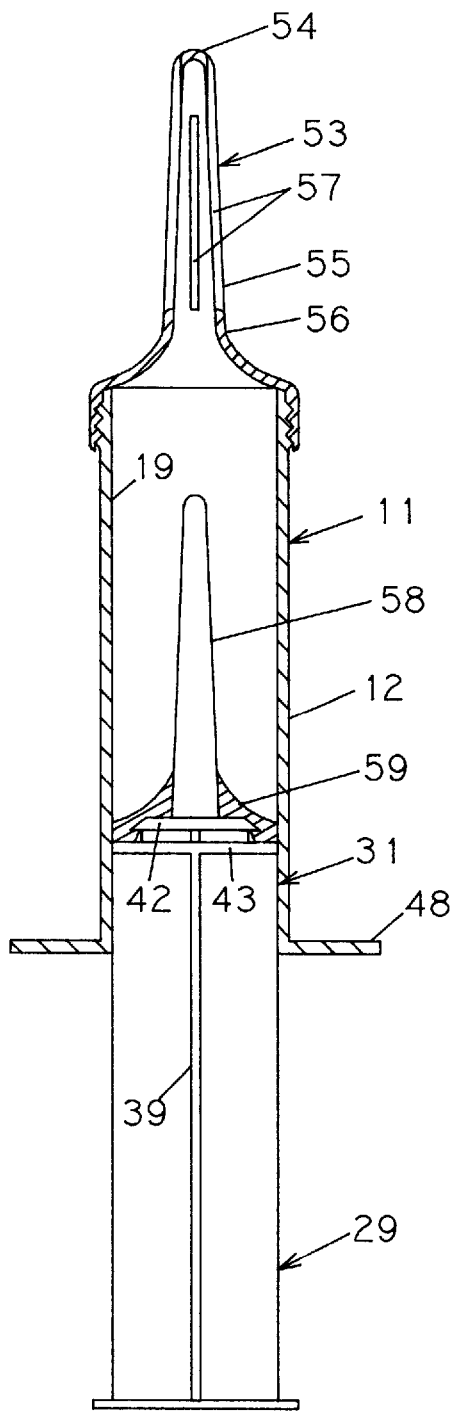
FIG. 7 is a cross-sectional view of a modified embodiment of a syringe in accordance with this invention.

FIG. 7 shows another embodiment of a syringe 11 modified particularly for use with infants and small children or in any case in which an area in a small cavity must be treated. This embodiment has a nozzle 53 with a rounded front end 54 and a wall 55 that is more sharply tapered and of smaller diameter, but may be longer, than the wall 15 of the nozzle 13 in FIG. 1. The wall 55 starts to flare out at a location 56, and the nozzle 53 is screwed onto the front end of the barrel 12 in the same way as the nozzle in FIG. 1.

The plunger 31 in FIG. 7 has a tapered nose 58 that is shaped according to the interior of the nozzle 53. The nose is so slender that, instead of forming it as a reinforced elastomeric member, as was the displacement part 30 in FIG. 1, the nose 58 is molded as part of the structure comprising the longitudinal flanges 36–39 and the transverse flanges 42 and 43. Only the base of the nose adjacent the flange 42 is encircled by an elastomeric ring 59 shaped to fit the interior surface of the flared part of the nozzle 53, and the nose and the ring, together, form a displacement part to force treatment fluid out through the slots 57. The ring 59 is gripped by the flanges 42 and 43 in the same manner as the displacement part 30 in FIG. 1.

Typical dimensions for the syringe in FIG. 7 differ from corresponding dimensions in FIG. 1 as follows: the diameter of the nozzle 13 in FIG. 1 might be between about 0.3" and about 0.35" at a location midway between the tip of the rounded end 14 and the location 16 at which it starts to flare out, while the diameter of the nozzle 53 in FIG. 7 might be between about 0.25" and about 0.3" at a location midway between the tip of the rounded end 54 and the location 56 at which it starts to flare out. The included angle of the wall 15 of the nozzle 13 might be between about 6°–12° while the wall 55 of the nozzle 53 might taper more sharply, at an included angle of between about 2°–6°. On the other hand, the length of the nozzle 13 from the tip of the rounded end 14 to the location 16 in the embodiment in FIG. 1 is between about 0.5" and about 1.0" while, in the embodiment in FIG. 7, the length of the nozzle 53 from the tip of the rounded end 54 to the location 56 is between about 0.7" and about 1.5". These dimensions are only examples and are not to be considered as limitations of the invention.

In other aspects, the nozzle 53 in FIG. 7 is similar to the nozzle 13 in FIG. 1.

Figure 8:
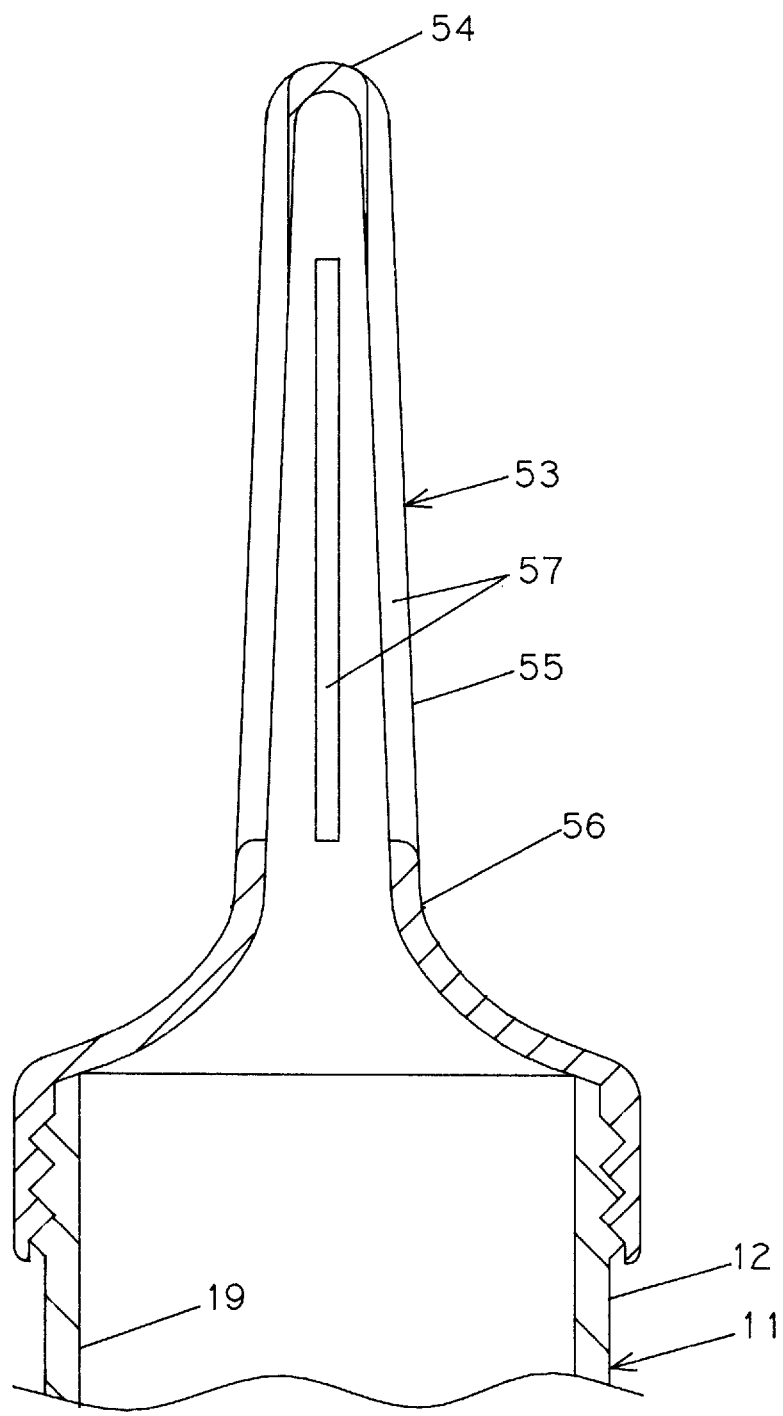
FIG. 8 is an enlarged, cross-sectional view of the nozzle of the syringe in FIG. 7.

FIG. 8 is an enlarged view of the nozzle 53, which shows that, because of the small included angle of the tapered wall 55, there are only four slots 57 in the nozzle 53. This still permits the blades of the mold forming these slots to be separated longitudinally from the nozzle. However, the diameter of the wall 55 is too uniform along its length to provide room for any bridges.

Figure 9:
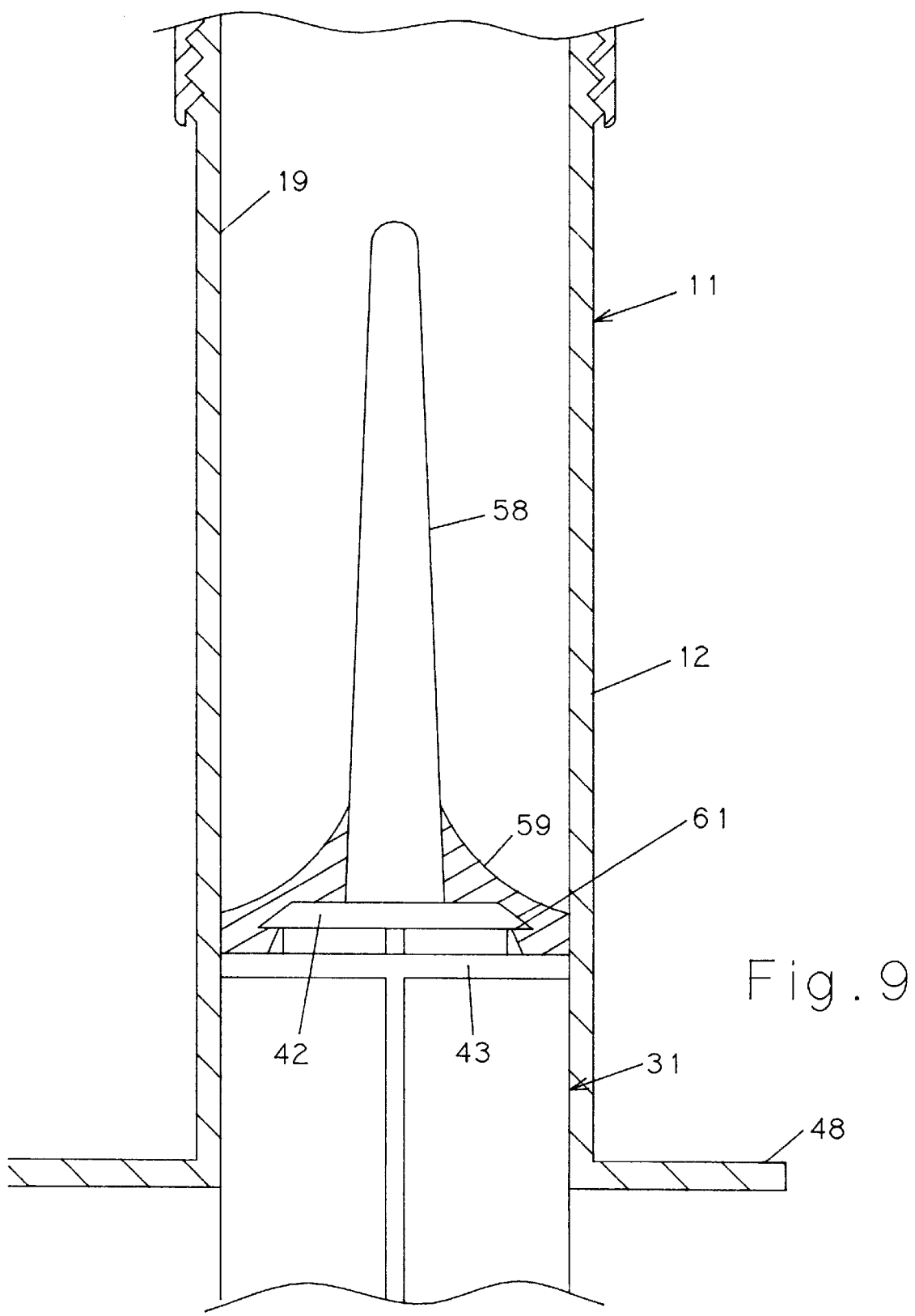
FIG. 9 is an enlarged, cross-sectional view of the front end of the plunger in FIG. 7.

FIG. 9 is an enlarged view of the front part of the plunger 31 showing the displacement part consisting of the nose 58 and the ring 59. The nose 58 moves with other parts of the plunger 31 because they are molded as a unitary structure. The ring 59 has an inwardly directed flange 61 that is pressed over the flange 42 and fits under it to secure the elastomeric ring to the rest of the plunger.

Figure 10:
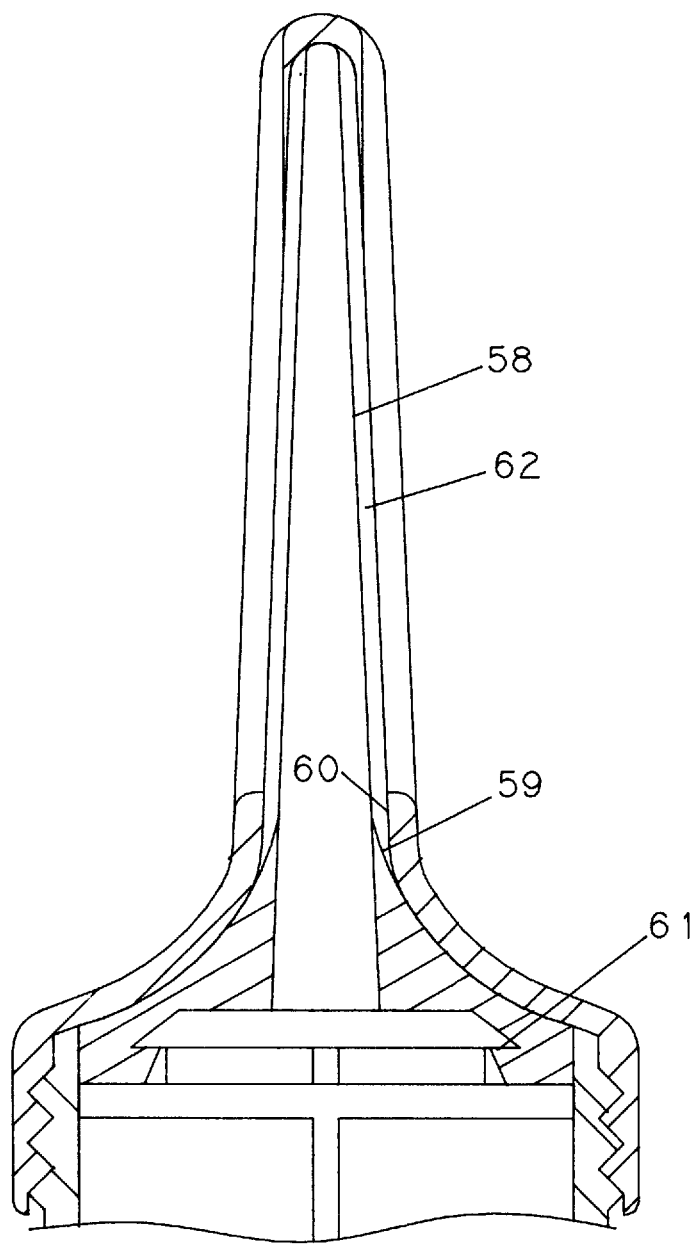
FIG. 10 is an enlarged, cross-sectional view showing the way the plunger in FIG. 9 fits into the nozzle in FIG. 8.

FIG. 10 show the relation between the nose 58 and the internal surface 60 of the nozzle when the plunger has been pushed forward as far as it will go so that the tip of the nose is in contact with the inner surface of the rounded end of the nozzle to expel substantially all of the treatment fluid. The dimensions have been exaggerated to show a gap 62 between the side of the nose and the surface 60. Typically, this gap would be only between about 0.005" and about 0.015" and would retain only a very thin film of the treatment fluid, not enough to affect the fact that the syringe dispenses substantially all of a selected quantity of treatment fluid.

The invention has been described in terms of a specific embodiment, but it will be apparent to those skilled in the technology with which this invention deals that the concept may be embodied in other forms without departing from the true scope of the invention.

What is claimed is:

1. A syringe for dispensing a selected amount of a treatment fluid against a side wall surface of a body cavity to treat a pathological condition of the side wall surface, the syringe comprising:
   (a) a generally cylindrical barrel having first and second ends spaced apart along the axis of the barrel, the first end having an internal surface of a certain internal cross-sectional configuration and size and an end surface of a certain configuration;
   (b) a nozzle having:
      (i) first and second ends spaced apart along a nozzle axis by a predetermined distance, the external surface of the first end being smoothly rounded and having a relatively small perimeter perpendicular to the nozzle axis to facilitate entry of the first end of the nozzle into the cavity, the second end being open and having a larger perimeter than the rounded first end,
      (ii) a side wall having inner and outer surfaces, the inner surface enclosing, between the first and second ends of the nozzle, a cross-sectional area that increases with increasing distance from the first end of the nozzle toward the second end thereof, the nozzle also having, adjacent the open second end, an intersecting surface that has, at a predetermined distance along the nozzle axis from the rounded first end, a configuration that substantially matches the configuration of the end surface of the barrel, and
      (iii) side aperture slots through the sidewall of the nozzle, each of the slots having side edges substantially parallel to the nozzle axis and one end closer to the first end of the nozzle;
   (c) attachment means to attach the nozzle releasably to the barrel with the intersecting surface of the nozzle in substantially fluid-tight contact with the first end of the barrel; and
   (d) a plunger movable longitudinally along the barrel and having:
      (i) a front portion facing the nozzle and shaped to fit the inner surface thereof, the front end of the plunger forming, with the inner surface of the nozzle and a portion of the barrel adjacent the first end thereof, a chamber into which the selected amount of the treatment fluid can be placed, and
      (ii) actuator means to push the front portion of the plunger fully into the nozzle to fit against the inner surface thereof and thereby fill the chamber and displace substantially all of the treatment fluid through the side aperture slots.

2. A syringe according to claim 1 in which each of the slots has an end surface closer to the front end of the nozzle, and that end surface is substantially parallel to the nozzle axis.

3. A syringe according to claim 1 in which the barrel is round and has a circular internal configuration of a certain diameter.

4. A syringe according to claim 1 in which the nozzle has a substantially hemispherical front end.

5. A syringe according to claim 4 in which the nozzle has closed front end.

6. A syringe according to claim 1 in which the sidewall of the nozzle is continuously tapered outwardly from the rounded first end to a location between the first end and the open second end.

7. A syringe according to claim 6 in which the sidewall of the nozzle flares out increasingly between said location and the second end.

8. A syringe according to claim 1 in which the sidewall of the nozzle has uniform thickness between the slots.

9. A syringe according to claim 1 in which the attachment means comprises interfitting surfaces adjacent the second end of the nozzle and first end of the barrel.

10. A syringe according to claim 1 in which the attachment means comprises interfitting threads at the second end of the nozzle and first end of the barrel.

11. A syringe according to claim 1 in which the plunger comprises a front portion shaped to conform substantially to the inner surface of a portion of the nozzle in which the slots are located.

12. A syringe according to claim 11 in which the plunger comprises an elongated actuator with first and second axially spaced flanges, and the front portion comprises generally hollow elastomeric means having a flange that extends inwardly between the first and second axially spaced flanges.

13. A syringe according to claim 11 in which the actuator has a relatively rigid front end that extends into the elastomeric portion to provide stiffening thereof.

14. A syringe for injecting a selected amount of a treatment fluid into a body cavity that includes a side wall surface to be treated by the fluid, the syringe comprising:
   (a) a barrel having:
      (i) first end and second ends spaced apart along an axis,
      (ii) a first end surface of a certain configuration, and
      (iii) an internal surface of a certain configuration and size along its length;
   (b) a nozzle having:
      (i) a smoothly rounded first end having a relatively small circumference to facilitate entry into the cavity,
      (ii) an open second end of larger circumference than the rounded first end and spaced a predetermined axial distance from the rounded end, (iii) an intersecting surface to abut the first end of the barrel, said intersecting surface having a configuration substantially matching the end surface of the barrel to fit fluid-tight against the end surface of the barrel, (iv) a side wall having inner and outer surfaces, the inner surface enclosing, between the first and second ends of the nozzle, a cross-sectional area that increases with increasing distance from the first end of the nozzle toward the second end thereof, and (v) side aperture slots through the sidewall of the nozzle, each of the slots having side edges substantially parallel to the axis of the nozzle; and (c) a plunger movable longitudinally along the barrel and defining, with the nozzle and a portion of the barrel adjacent the first end thereof, a chamber, whereby, when the plunger is drawn along the barrel in a direction away from the nozzle, the selected amount of the treatment fluid can be placed in the chamber, the plunger comprising:

(i) a front portion shaped to substantially conform to the inner surface of the nozzle, and (ii) means to push the front portion fully into the nozzle and against the inner surface of the nozzle to fill the chamber and displace substantially all of the treatment fluid through the side aperture slots.

15. The syringe of claim 14 in which the first end of the barrel and the first end of the nozzle have mating threads, whereby, when the nozzle is unscrewed from the barrel and the plunger is drawn into the barrel to open the chamber, the predetermined amount of the treatment fluid can be deposited in the chamber and the nozzle and the barrel can be screwed together thereafter.

16. The syringe of claim 14 comprising a plurality of bridges axially spaced apart along the nozzle, each of the bridges spanning a respective one of the slots.

17. The syringe of claim 16 in which each of the bridges has an outwardly facing surface inset relative to the outer surface of the side wall.

18. The syringe of claim 14 in which:

(a) the barrel comprises a rigid thermoplastic tube having a uniform internal cross-sectional configuration;

(b) the nozzle comprises a rigid thermoplastic shell having a closed second end; and (c) the plunger comprises rigid thermoplastic actuator means to push the front portion fully into the nozzle.

19. The syringe of claim 14 in which: the cross-sectional area of the nozzle increases smoothly with increasing distance from the first end of the nozzle toward the second end thereof.

* * * * *